US008466437B2

(12) United States Patent
Boettiger

(10) Patent No.: US 8,466,437 B2
(45) Date of Patent: *Jun. 18, 2013

(54) HIGH RESOLUTION FLUORESCENCE DETECTION SYSTEM

(75) Inventor: Ulrich Boettiger, Garden City, ID (US)

(73) Assignee: Aptina Imaging Corporation, George Town (KY)

( * ) Notice: Subject to any disclaimer, the term of this patent is extended or adjusted under 35 U.S.C. 154(b) by 106 days.

This patent is subject to a terminal disclaimer.

(21) Appl. No.: 13/165,005

(22) Filed: Jun. 21, 2011

(65) Prior Publication Data
US 2012/0273695 A1    Nov. 1, 2012

Related U.S. Application Data

(60) Provisional application No. 61/480,068, filed on Apr. 28, 2011.

(51) Int. Cl.
*F21V 9/16* (2006.01)
*H01L 27/146* (2006.01)
*G01T 1/20* (2006.01)

(52) U.S. Cl.
USPC ............ 250/459.1; 250/458.1; 250/370.09; 250/370.11

(58) Field of Classification Search
None
See application file for complete search history.

(56) References Cited

U.S. PATENT DOCUMENTS

| | | | |
|---|---|---|---|
| 5,943,129 A | 8/1999 | Hoyt | |
| 6,359,284 B1 * | 3/2002 | Hayashi et al. | 250/458.1 |
| 7,442,973 B2 * | 10/2008 | Komoguchi et al. | 257/291 |
| 7,531,443 B2 | 5/2009 | Pratt | |
| 2009/0279093 A1 * | 11/2009 | Van Herpen et al. | 356/417 |
| 2010/0065726 A1 * | 3/2010 | Zhong et al. | 250/227.24 |
| 2010/0111762 A1 * | 5/2010 | Cho | 422/52 |
| 2012/0061587 A1 * | 3/2012 | Wu et al. | 250/459.1 |
| 2012/0223214 A1 * | 9/2012 | Lee et al. | 250/208.1 |

OTHER PUBLICATIONS

Cui et al., "Lensless high-resolution on-chip optofluidic microscopes for *Caenorhabditis elegans* and cell imaging" [online], May 2008 [retrieved on May 11, 2011]. Retrieved from the Internet: http://www.biophot.caltech.edu/publications/pdf/2008-OFM-ONAS.pdf.

(Continued)

*Primary Examiner* — David Porta
*Assistant Examiner* — Jeremy Valentiner
(74) *Attorney, Agent, or Firm* — David C. Kellogg

(57) ABSTRACT

A compact image sensor for imaging radiation emitted by fluorescing objects exposed to excitation light is disclosed. The compact image sensor includes a light guide defining a longitudinal axis for channeling radiation emitted by the fluorescing object; a reflective surface defined on the light guide that is oriented at an angle with respect to the longitudinal axis of the light guide to reflect the excitation light away from a detector of the image sensor; and the detector positioned at an end of the light guide for imaging radiation emitted by the fluorescing object. Also disclosed is a fluorescence imaging system for imaging radiation emitted by a fluorescing object to be imaged by compact image sensor and a method of fluorescence imaging.

20 Claims, 2 Drawing Sheets

OTHER PUBLICATIONS

Cui et al., "Quantitative differential interference contrast microscopy based on structured-aperture interference" [online], Sep. 2008 [retrieved on May 11, 2011]. Retrieved from the Internet: http://www.biophot.caltech.edu/publications/pdf/Cui-APL-2007-DIC.pdf.

Wu et al., "The application of Fresnel zone plate based projection in optofluidic microscopy" [online], Sep. 2008 [retrieved on May 11, 2011]. Retrieved from the Internet: http://www.biophot.caltech.edu/publications/pdf/Wu-OE-2008-Fresnel.pdf.

Hutto et al., U.S. Appl. No. 13/105,232, filed May 11, 2011.

Boettiger et al., U.S. Appl. No. 13/188,811, filed Feb. 12, 2013.

* cited by examiner

HIGH RESOLUTION FLUORESCENCE DETECTION SYSTEM

CROSS REFERENCE TO RELATED APPLICATIONS

This application claims priority of U.S. Provisional Patent Application Ser. No. 61/480,068, filed Apr. 28, 2011, which is incorporated by reference.

TECHNICAL FIELD

The present invention relates to a fluorescence imaging system.

BACKGROUND OF THE INVENTION

As disclosed in U.S. Pat. No. 5,943,129, which is incorporated by reference herein, in fluorescent imaging, a sample is illuminated with excitation light of one wavelength while a resulting fluorescent emission at a second, typically longer wavelength is imaged. Because the fluorescent efficiency of many samples is low, i.e. typically 1 photon of fluorescent emission or less per 100 photons of excitation, the optical imaging system must efficiently collect the weak fluorescent emission without interference from the much stronger excitation signal. The optical system must provide an efficient optical path for delivering fluorescent emission light to the imager, with little or no such path for excitation light. Typically, spectral filters, such as colored-glass or interference filters, are used to provide at least some degree of the required wavelength selectivity. Disclosed herein is a low-profile sensor device that provides an efficient optical path for delivering emission light to the imager and a method for operating the device.

BRIEF DESCRIPTION OF THE FIGURES

The invention is best understood from the following detailed description when read in connection with the accompanying drawing. It is emphasized that, according to common practice, the various features of the drawing are not to scale. Included in the drawing are the following figures.

DETAILED DESCRIPTION OF THE INVENTION

Figure 1:
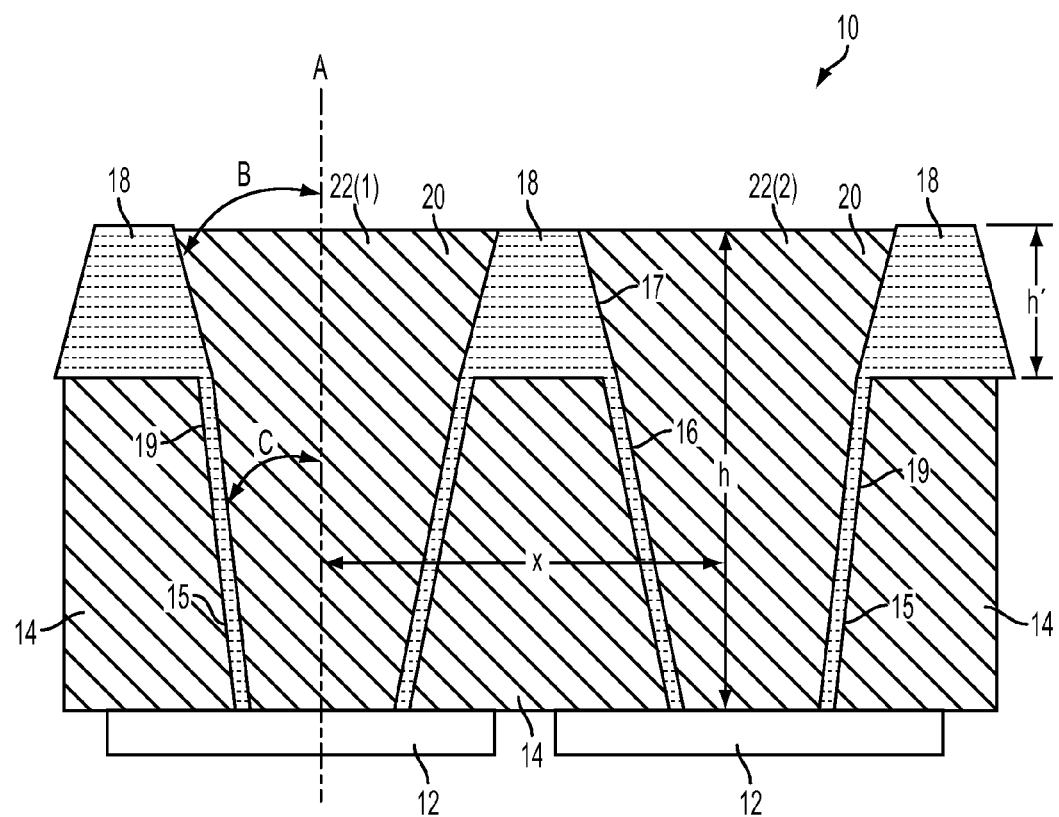
FIG. 1 depicts a cross-sectional view of the image sensor, shown schematically, according to one exemplary embodiment of the invention.

This invention will now be described with reference to several embodiments selected for illustration in the drawings. It will be appreciated that the scope and spirit of the invention are not limited to the illustrated embodiments.

The term "excitation light source" as used herein refers to a source of irradiance) that can provide excitation that results in fluorescent emission. Light sources can include, but are not limited to, white light, halogen lamp, lasers, solid state laser, laser diode, micro-wire laser, diode solid state lasers (DSSL), vertical-cavity surface-emitting lasers (VCSEL,), LEDs, phosphor coated LEDs, organic LEDs (OLED), thin-film electroluminescent devices (TFELD), phosphorescent OLEDs (PHOLED), inorganic-organic LEDs, LEDs using quantum dot technology, LED arrays, filament lamps, arc lamps, gas lamps, and fluorescent tubes. Light sources can have high irradiance, such as lasers, or low irradiance, such as LEDs. The different types of LEDs mentioned above can have a medium to high irradiance.

The term "detector" as used herein refers to any component, portion thereof, or system of components that can detect light including a photodiode, a photodiode array, a charged coupled device (CCD), a back-side thin-cooled CCD, a front-side illuminated CCD, a CCD array, a photo-multiplier tube (PMT), a PMT array, complimentary metal-oxide semiconductor (CMOS) sensors, CMOS arrays, a charge-injection device (CID), CID arrays, etc. The detector can be adapted to relay information to a data collection device for storage, correlation, and/or manipulation of data, for example, a computer, or other signal processing system.

The term "filter" as used herein refers to any electromagnetic radiation exclusion device that can operate at a particular wavelength or range of wavelengths. Filter includes optical filters. The filter material may be a pigment-based color filter or a dye-based color filter, or any combination thereof.

The term "fluorescing object" as used herein refers to any biological or chemical substance with components that can be excited by excitation light to emit fluorescent light or radiation.

FIG. 1 depicts a cross-sectional view of an image sensor 10, shown schematically, according to one exemplary embodiment of the invention. The image sensor 10 generally includes one or more detectors 12 (two shown), a substrate 14 defining two countersunk apertures 15 that are each positioned above and in radial alignment with a detector 12, a reflective layer 18 deposited on the top surface of the substrate 14 and within each aperture 15 of the substrate 14, and a plurality of filters 20 (two shown) each of which are deposited on the reflective surfaces 16 and 17 of the reflective layer 18 and at least a portion of the top surface of the detectors 12.

The image sensor 10 comprises light guide/pipe structures 22(1) and 22(2), which are referred to collectively as light guide/pipe structures 22 or pixels. Each light guide/pipe structure 22 comprises co-aligned reflective surfaces 16 and 17 and the filter material 20 that is deposited on the co-aligned reflective surfaces 16 and 17. The filters 20 are at least partially encapsulated within their respective light guides 22. The geometry of the reflective surface 16 is defined by the geometries of the substrate aperture 15 and the lining portion 19 of the reflective layer 18, whereas the geometry of each reflective surface 17 is dictated by the geometry of the counter sunk hole of the reflective layer 18 that forms the reflective surface 17.

The reflective surfaces 16 and 17 form acute angles with respect to a longitudinal axis 'A' of a respective light guide structure 22. The angle 'B' of each conically-shaped reflective surface 17 may be between 5 degrees and 30 degrees, for example, with respect to the longitudinal axis 'A' of a respective light guide structure 22. Alternatively, the angle 'B' may be between 20 degrees and 60 degrees, for example. The angle 'C' of each conically-shaped reflective surface 16 may be between 0 degrees and 10 degrees, for example, with respect to the longitudinal axis 'A' of a respective light guide structure 22. Although not explicitly shown, the angle 'C' could also be between −5 degrees and 0 degrees. According to one aspect of the invention the reflective surfaces 16 and 17 are discontinuous and the angles 'B' and 'C' are different, while according to another aspect of the invention, the reflective surfaces 16 and 17 are continuous and the angles 'B' and 'C' are the same.

The top portion of the reflective layer 18, which is bounded by height h', may be a separate component from the lining portion 19 of the reflective layer 18. In addition to being solid metal or other reflective film(s), the top portion of the reflective layer 18 could also consist of a metallized core.

The surfaces 16 and 17 of each light guide structure 22 do not have to be symmetrical about longitudinal axis A, as shown. The surface that faces the incoming light (i.e., the left-side surfaces of each light guide structure) should be angled to reflect excitation light, however, the remaining surfaces of the light guide/pipe structures 22 may not be angled, and may be vertical, for example.

According to this exemplary embodiment, the detectors 12 are photodiodes, the reflective layer 18 is composed of Aluminum, the substrate 14 is composed of a dielectric material, such as Silicon Oxide, or a cross-linked polymer, and each filter 20 is composed of a red-color filter material. Those of ordinary skill in the art will recognize that other materials may be used, as described previously, without departing from the scope of the invention.

Figure 2:
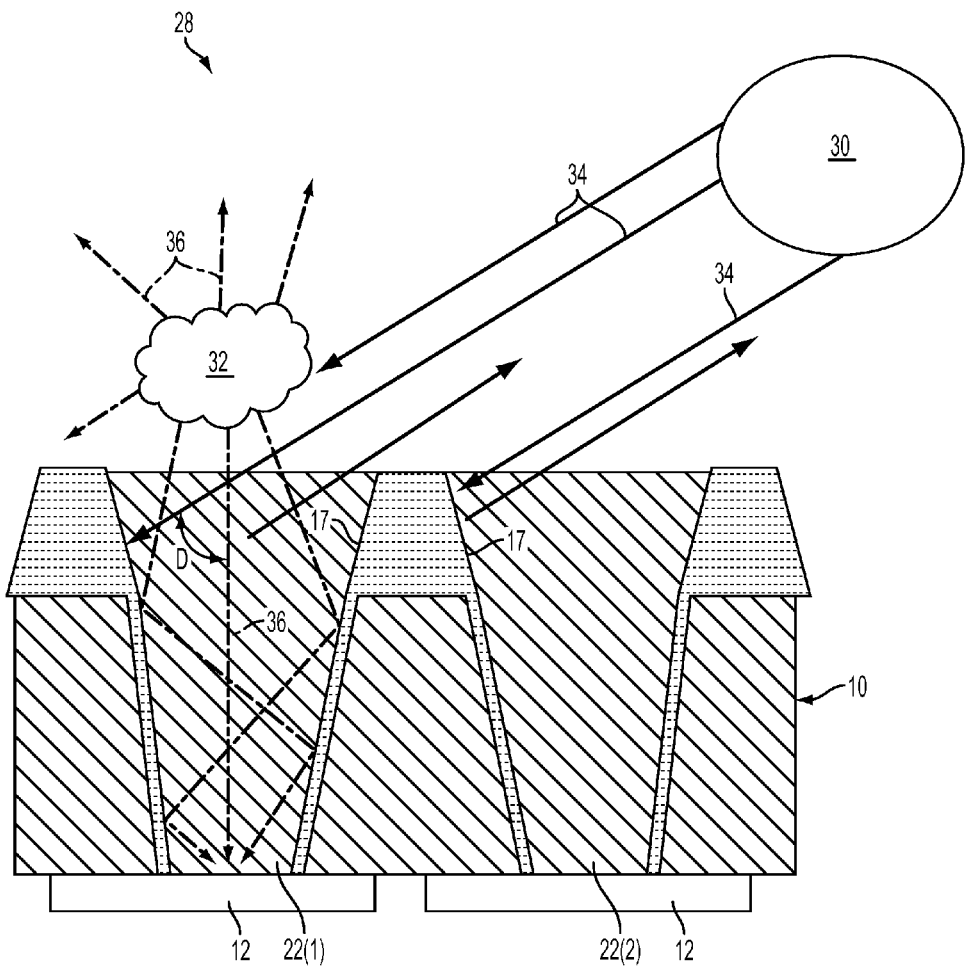
FIG. 2 depicts a schematic diagram of a fluorescence imaging system including the image sensor of FIG. 1 shown in cross-section.

FIG. 2 is a schematic diagram of a fluorescence imaging system 28 including the image sensor 10 of FIG. 1. The fluorescence imaging system 28 generally includes an excitation light source 30 and the sensor 10. According to one exemplary method of operating the fluorescence imaging system 28, the excitation light source 30 is positioned at an elevation above the top surface of the image sensor 10 and is laterally spaced from the sensor 10 and the fluorescing object 32 by a predetermined distance. The fluorescing object 32 is positioned either on or in very close proximity to the top surface of the sensor 10. The fluorescing object 32 can be a component of a liquid or film deposited on a surface of the sensor 10.

The excitation light source 30 produces excitation light beams 34 which can be collimated. Illuminating the fluorescing object 32 with the excitation light beams 34 causes the fluorescing object 32 to fluoresce, i.e., emit radiation 36. Some of the radiation 36 is directed vertically downwards through one or more filters 20 of the sensor 10 (see broken line arrows) and onto the top surface of one or more detectors 12 which detect the radiation 36. The one or more detectors 12 receive and image the radiation 36 emitted from the fluorescing object 32. The one or more detectors 12 are adapted to relay the image information to a data collection device for storage, correlation, and/or manipulation of data, for example, a computer, or other signal processing system.

Because the excitation light source 30 is laterally spaced from the light guides 22 of the sensor 10 by a predetermined distance, the excitation light beams 34 produced by the light source 30 are oriented with respect to the longitudinal axis 'A' of the light pipes 22 by a predetermined angle 'D.' The angle 'D' may be 35 degrees to 55 degrees, for example. The value of the predetermined angle 'D' is defined by the respective physical locations of the excitation light source 30 and the sensor 10.

Angling the excitation light source 30 with respect to the light guides 22 by angle 'D' is referred to herein as angled illumination. By virtue of angled illumination, the bulk of the incoming excitation light beams 34 reflect off of the angled reflective surfaces 16 and 17 of the light guides 22 in a direction away from the sensor 10. Thus, the detectors 12 do not detect the reflected excitation light beams 34. Reflecting the excitation light beams 34 minimizes the ratio of excitation light to fluorescent light (i.e., radiation) that is detected by the detector 12. This ratio is commonly referred to as the suppression ratio.

In many conventional fluorescence imaging systems, the excitation light source is positioned directly above the light guides and the light guides are straight channels without angled walls. In those conventional sensor systems, the height of the filter material must be sufficiently large to filter the incoming excitation light beams in order to achieve a fixed suppression ratio requirement for a particular application. By contrast, the height 'h' of the filter 20, and, consequently, the height of the sensor 10, is minimized because the reflective surfaces 16 and 17 reflect the bulk of the unwanted incoming excitation light beams 34. Thus, the height 'h' of the sensor 10 can be smaller than the height of sensors of conventional fluorescence imaging systems. The height 'h' of the sensor 10 can be comparatively reduced by 30-50% while achieving the same suppression ratio and signal to noise ratio as the aforementioned conventional sensor. By reducing the height 'h' of the sensor 10, the pixel pitch 'x' (see FIG. 1) can be reduced allowing to either shrink the sensor size for a given number of pixels or to increase the number of active pixels for a given sensor array size.

Applications for the fluorescence imaging system 28 include, but are not limited to, any micro fluidic, lab-on-chip applications that use fluorescence spectroscopy for analysis of the properties of samples that are brought in close proximity to the entrance pupil of the image sensor pixel.

According to one exemplary method of fabricating the image sensor 10 of FIGS. 1 and 2, the substrate 14 is first formed by a CVD oxide deposition process. The thickness of the substrate 14 may be 3-4 micrometers, for example. A lithography process patterns holes over each detector 12 or every other detector 12 or any other combinations. A dry etch process creates the apertures 15 in the substrate 14. The etch can be adjusted to obtain any desired taper. A resist strip process is employed to remove the resist and clean the surface for better adhesion to subsequent layers.

By way of a PVD deposition process, Aluminum or other metal or metals form the reflective layer 18 that is applied over the substrate 14 and within the apertures 15 of the substrate 14. The thickness of the metal could be 0.5 microns to 2 microns, for example, on the surface of substrate 14. The corresponding thickness of the lining portion 19 may be 300-700 Angstroms, for example, which can be adjusted by the metal deposition process. A dry etch process clears metal from the bottom of the substrate 14. A dual etch process may be performed to clear the bottom in one step and then clear the substrate streets and bond pads with another step (for example a wet metal etch while keeping the light guides covered with resist). A single etch may also be performed with adequate etch controls.

The filter layer 20 is then spin coated to fill the light guides 22 and also form an additional layer over the light guides 22 if desired. This may be done in multiple layers or in a single layer. This may be photo-definable or not. A planarization step (e.g., chemical-mechanical planarization) may be employed to planarize the filter layer. A chemical vapor deposition (CVD) oxide or other dielectric layer(s) deposition passivates the filter layer and can further tailor the optical filtering properties of the filter layer. A lithography process patterns the passivation and the filter layer. A dry etch process clears the passivation and the filter layer from the bond pads and the scribe lanes. A resist strip process removes the resist.

Although the invention is illustrated and described herein with reference to specific embodiments, the invention is not intended to be limited to the details shown. Rather, various modifications may be made in the details within the scope and range of equivalents of the claims and without departing from the spirit of the invention.

What is claimed:

1. A compact image sensor for imaging radiation emitted by a fluorescing object that is exposed to excitation light comprising:

a light guide defining a longitudinal axis for channeling radiation emitted by the fluorescing object;

a reflective surface defined on the light guide that is oriented at an angle with respect to the longitudinal axis of the light guide to reflect the excitation light away from a detector of the image sensor, wherein the reflective surface has a frusto-conical shape; and the detector positioned at an end of the light guide for imaging radiation emitted by the fluorescing object.

2. The compact image sensor of claim 1 further comprising an array of light guides disposed in the compact image sensor.

3. The compact image sensor of claim 1, wherein the angle defined between the reflective surface and the longitudinal axis of the light guide is between 5 degrees and 60 degrees.

4. The compact image sensor of claim 1, wherein the compact image sensor includes a substrate and a reflective layer formed over the substrate, wherein said reflective surface is defined on the reflective layer.

5. The compact image sensor of claim 4, wherein the substrate is composed of a dielectric material or a cross-linked polymer.

6. The compact image sensor of claim 1 further comprising filter material that is at least partially encapsulated within the light guide for filtering the excitation light and passing the radiation emitted by the fluorescing object.

7. The compact image sensor of claim 6, wherein the filter material is positioned directly above the detector.

8. The compact image sensor of claim 1, wherein the detector is a photodiode.

9. A fluorescence imaging system for imaging radiation emitted by a fluorescing object to be imaged by the system through fluorescing of the fluorescing object in response to illumination of the fluorescing object by excitation light, said system comprising:

an excitation light source operable for emitting collimated excitation light; and a compact image sensor for imaging radiation emitted by the fluorescing object that is exposed to excitation light, said compact image sensor comprising a light guide having a reflective surface that is oriented at an angle with respect to a longitudinal axis of the light guide;

wherein the excitation light source is positioned at an elevation above the compact image sensor and a position that is laterally offset from the light guide such that incident excitation light emitted by the excitation light source is at least partially reflected away from the image sensor by the reflective surface of the light guide.

10. The fluorescence imaging system of claim 9 further comprising an array of light guides disposed in the compact image sensor.

11. The fluorescence imaging system of claim 9 further comprising a detector positioned at an end of the light guide for imaging radiation emitted by the fluorescing object.

12. The fluorescence imaging system of claim 11, wherein the detector is a photodiode.

13. The fluorescence imaging system of claim 9, wherein the compact image sensor includes a substrate and a reflective layer formed over the substrate, wherein said reflective surface is defined on the reflective layer.

14. The fluorescence imaging system of claim 9 further comprising filter material that is at least partially encapsulated within the light guide for filtering the excitation light and passing the radiation emitted by the fluorescing object.

15. The fluorescence imaging system of claim 14, wherein the filter material is a pigment-based color filter, a dye-based color filter, or both a pigment-based color filter and a dye-based color filter.

16. The fluorescence imaging system of claim 9, wherein the angle defined between the reflective surface and the longitudinal axis of the light guide is between 5 degrees and 60 degrees.

17. The fluorescence imaging system of claim 9, wherein the reflective surface has a frusto-conical shape.

18. A method of fluorescence imaging comprising the step of directing excitation light toward an object that is positioned either on or in close proximity to a compact image sensor including a light guide having a reflective surface that is oriented at an angle with respect to a longitudinal axis of the light guide, wherein the excitation light causes the object to fluoresce while incident excitation light is at least partially reflected away from the image sensor by the angled reflective surface of the light guide.

19. The method of claim 18, wherein the light guide directs radiation emitted by a fluorescing object toward a detector that is mounted on or adjacent the light guide.

20. The method of claim 18 further comprising the step of filtering the excitation light using a filter that is at least partially encapsulated by the light guide.

* * * * *